United States Patent [19]
Hoeller

[11] Patent Number: 5,671,061
[45] Date of Patent: Sep. 23, 1997

[54] METHOD AND APPARATUS FOR ASSESSING THE EFFECT OF YARN FAULTS ON WOVEN OR KNITTED FABRICS

[75] Inventor: Robert Hoeller, Uster, Switzerland

[73] Assignee: Zellweger Luwa AG, Uster, Switzerland

[21] Appl. No.: 531,485

[22] Filed: Sep. 21, 1995

Related U.S. Application Data

[63] Continuation-in-part of Ser. No. 77,682, Jun. 16, 1993, abandoned.

[30] Foreign Application Priority Data

Jun. 18, 1992 [CH] Switzerland ............ 01 926/92

[51] Int. Cl.$^6$ .............. G06F 15/46; G01N 21/89
[52] U.S. Cl. .......... 356/429; 250/562; 250/559.24; 250/559.46; 356/430; 356/238
[58] Field of Search ............... 356/429, 430, 356/238, 431; 250/562, 563, 559.24, 559.46

[56] References Cited

U.S. PATENT DOCUMENTS

| | | | |
|---|---|---|---|
| 4,744,035 | 5/1988 | Hashim | 257/559.46 |
| 4,857,747 | 8/1989 | Bolton et al. | 250/559 |
| 4,887,155 | 12/1989 | Massen | 250/559.24 |
| 4,953,400 | 9/1990 | Bossuyt | 356/238 |
| 4,984,181 | 1/1991 | Kliman et al. | 364/518 |
| 5,015,867 | 5/1991 | Siegel et al. | 250/559.24 |
| 5,030,841 | 7/1991 | Wampfler | 356/429 |
| 5,130,559 | 7/1992 | Leifeld et al. | 250/562 |
| 5,146,550 | 9/1992 | Furter et al. | 364/470 |
| 5,178,008 | 1/1993 | Aemmer | 364/470 |
| 5,283,623 | 2/1994 | Muhlberg et al. | 356/238 |
| 5,351,308 | 9/1994 | Klaminer et al. | 356/430 |

FOREIGN PATENT DOCUMENTS

| | | |
|---|---|---|
| 0 199 552 | 10/1986 | European Pat. Off. . |
| 0 439 659A1 | 2/1990 | European Pat. Off. . |
| 2 192 722 | 11/1990 | United Kingdom . |

OTHER PUBLICATIONS

Pages from "Evenness Testing in Yarn Production: Part I" by R. Furter, The Textile Institute, 1982, Uster Tester, pp. 60–64, Title Page and Table of Contents.

"System for creating a fault diagnosis on production machines and application of the system on textile machines" Zellweger Uster AG, CH–8610, PA–4PG/210 pp. 1–28, believed to correspond to Swiss Patent Application 2651/91.

"Measurement of the trash particle content of yarns", Inge Stockert, ITMA 91, Hannover Sep. 24–Oct. 3, 1991, ITB Yarn Forming Apr. 1992, Title page and pp. 23–26.

"Test methods for evenness measurement of card webs", Leifeld, Yarn Forming Jan. 1995, pp. 57–63 and 66.

"The third dimension in surface geometry . . . ", Micro–Topographer 200 System, Dec. 1984, Federal Products Corporation, 5 sheets.

"Textile Laboratory Manual" Walter Garner, 1951, Chemical Publishing Co., Inc., pp. 167–169 and title page.

"Basic and Practice of The Evenness Testing", Keisokki Kogyo Co., Ltd., Apr. 1986, pp. 3–5 and pp. 67–69.

*Primary Examiner*—Robert P. Limanek
*Assistant Examiner*—Alexander Oscar Williams
*Attorney, Agent, or Firm*—Burns, Doane, Swecker & Mathis, L.L.P.

[57] ABSTRACT

The assessment of the effects of yarn faults is carried out by simulating the fabric image. In a first step, the yarn is examined by a measuring member for parameters associated with the volume and/or the surface. In a second step, these parameters are converted into grey values or color values, and these values are assigned to image spots. Finally, the image spots are reproduced on a video display unit and/or a printer. An image is generated thereby, representing a simulation of a woven or knitted fabric produced from the examined yarn.

36 Claims, 3 Drawing Sheets

5,671,061

METHOD AND APPARATUS FOR ASSESSING THE EFFECT OF YARN FAULTS ON WOVEN OR KNITTED FABRICS

RELATED APPLICATIONS

The present application is a continuation-in-part application of U.S. application Ser. No. 08/077,682, entitled "METHOD AND APPARATUS FOR ASSESSING THE EFFECT OF YARN FAULTS ON WOVEN OR KNITTED FABRICS" filed Jun. 16, 1993 abandoned, the disclosure of which is hereby incorporated by reference in its entirety.

FIELD OF THE INVENTION

The present invention relates to a method and an apparatus for assessing the effect of yarn faults on woven or knitted fabrics produced from the respective yarn by simulation of the fabric image.

BACKGROUND

Traditional methods of this type use so-called display boards for simulating the fabric image. The respective yarn is wound spirally around trapezoidal or rectangular pieces of cardboard or metal sheets, thereby forming a kind of quasi woven or knitted fabric, from which possible fault patterns can be seen clearly. The display boards are therefore a valuable aid in estimating whether and to what extent a particular yarn is suitable for a particular fabric, and they allow predictions to be made on one of the most important quality features of the finished product, namely its appearance.

However, the production of the display boards by the winding of yarn around metal sheets is relatively labor intensive and is also no longer in keeping with the times, so that there is a need for a new method for simulating the fabric image. This new method should necessitate as little outlay as possible in terms of labor, it should be flexible and it should give reliable and reproducible results.

SUMMARY OF THE INVENTION

According to the invention, the following steps are carried out to assess the effects of yarn faults on the appearance of fabrics containing such yarns:

a. examination of the yarn for parameters associated with the volume and/or the diameter and/or the surface;

b. conversion of said parameters into grey values or color values and assignment of these values to image spots; and c. reproduction of the image spots to produce an image which represents a simulation of a woven or knitted fabric produced from the examined yarn.

An apparatus according to the invention is characterized by a measuring member for determining parameters associated with the volume and/or the surface of the yarn, by a computer for converting said parameters into grey or color values, by means for assigning the grey or color values to image spots, by a video display unit and/or a printer, and by control means for reproducing the image spots on the video display unit and/or on the printer for the purpose of simulating a woven or knitted fabric produced on the examined yarn.

By means of the invention, therefore, the display boards are produced electronically, and if a uniformity tester, such as, for example, the testers sold by Zellweger Uster AG under the designation USTER TESTER (USTER being a registered trademark of Zellweger Uster AG), is used as a measuring device for examining said parameters, the electronic display boards are calculated from the data conventionally produced. With the USTER TESTER, which is described by way of example in EP-A-0 249 741 and in CH-A-671 105 (the disclosures of both of which are incorporated herein by reference), the uniformity and/or the hairiness of a yarn sample among other things are examined and are represented in the form of a graph, a wavelength spectrum or other graphical representations of the variations of the measured parameters on a video display unit and/or on a printer. Uniformity and hairiness are two parameters which are essential for the later fabric image and which can be processed at a relatively low outlay in terms of software in order to simulate the display boards.

BRIEF DESCRIPTION OF THE DRAWINGS

The invention is explained in more detail below by means of an exemplary embodiment and the drawings in which.

DETAILED DESCRIPTION OF THE PREFERRED EMBODIMENTS

Figure 1:
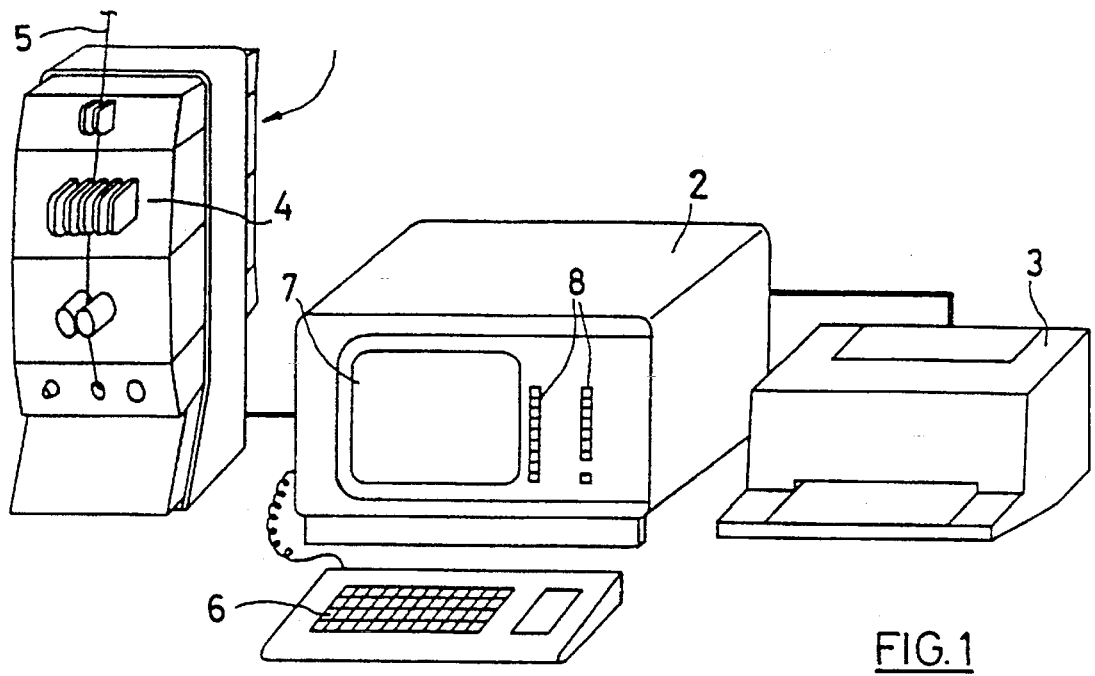
FIG. 1 shows a perspective representation of a test installation for determining the mass variations of a textile test material.

The test installation illustrated in FIG. 1 is the USTER TESTER of Zellweger Uster AG, which is used for determining material and quality characteristics of textile test material, such as, for example, yarns. These characteristics are, for example, mass variations, hairiness or structure (twist) of the examined yarn. See, in this respect, for example, CH-A-671 105, EP-A-0 249 741 and U.S. Pat. No. 5,030,841 (the disclosures of which are each incorporated herein by reference). Faults in these characteristics have an undesirable effect on the finished textile product.

The test installation includes, in known fashion, the actual test appliance 1, an evaluation and operating unit 2 and a printer 3. The test appliance 1 is provided with one or more measuring modules 4 which have measuring members for the characteristics to be examined. The test material or yarn designated by the reference symbol 5 is transported through the measuring members which continuously measure the mass, hairiness and/or structure and convert them into electrical signals. The tested yarn 5 is sucked off after the measurement.

The signal and data processing and the functional checking of the test installation are carried out in the evaluation and operating unit 2. Variables, measuring conditions and the desired representation of the results are entered via a keyboard 6, a video display unit 7 and control keys 8, and the measuring cycle and results appear in numerical and graphic form on the video display unit 7. The printer 3 likewise serves for the output of measured values and of graphic representations and especially also for the output of complete test reports.

Figure 2:
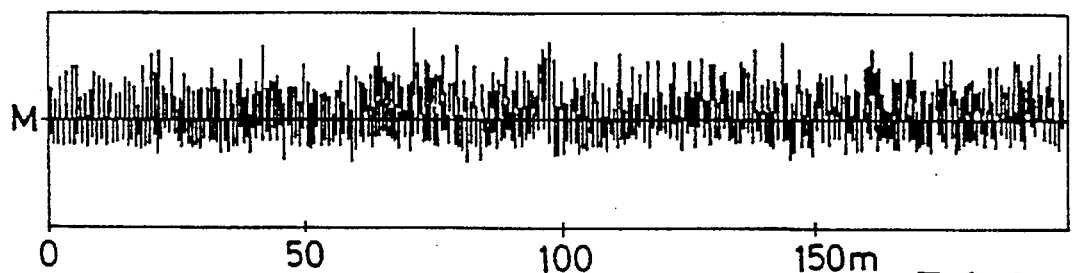
FIG. 2 shows a graph of an individual sample obtained by means of the test installation of FIG. 1.

The direct result of the examination of a yarn sample 5 by the test installation shown is the exemplary graph which is illustrated in FIG. 2 and which indicates the variations of the examined characteristics over the length of the test material. If, for example, the hairiness is being examined, this is defined as the total length of the fibers projecting from the yarn body, within a specific length of measuring field (that is, for example, a specific length of the yarn). The hairiness of a yarn is then the average value of the total lengths of fibers formed over the entire test length.

The FIG. 2 graph shows the variations of the examined characteristics around an average value M which corresponds to a standardized value of the signal representing the yarn cross-section. The spread or standard deviation can be calculated from these variations which, for example, are given in percentages when the mass variations are being examined and in absolute values when the hairiness is being measured.

Figure 3:
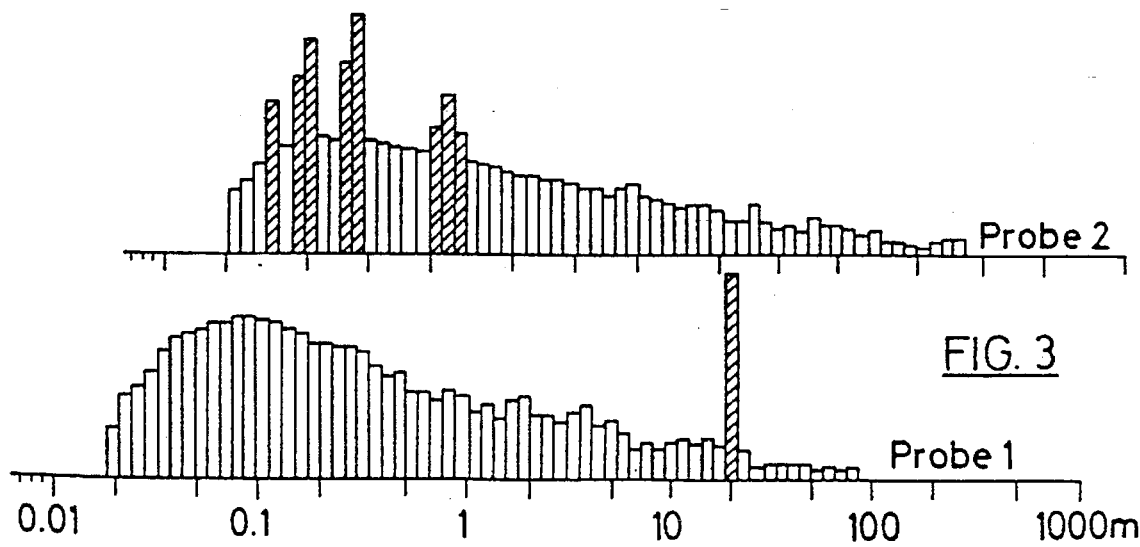
FIG. 3 shows an excerpt from a composite graphic chart with spectrograms of two samples.

Variations exceeding specific limits are an indication of a fault, and in the faults a distinction is made in a known way between periodic and non-periodic faults. By definition, periodic faults have a specific wavelength and can be detected in a simple way by means of the wavelength spectrogram, wherein spikes or "chimneys" which occur in the spectrogram indicate a fault. FIG. 3 shows the spectrograms of the mass variations of 2 samples; sample 1 has a chimney with a wavelength of 20 m and sample 2 has four chimneys which are in the range below 50 cm.

Depending on the width of the subsequent woven or knitted fabric and depending on the wavelength of the periodic fault, undesirable patterns occur in the finished product and often make the finished product useless. Reference may be made, in this respect, to the publication "Evenness Testing in Yarn Production: Part I" by R. Furter, The Textile Institute, 1982, in which the influence of periodic mass variations on woven and knitted fabrics is explained on page 60 ff. These explanations reveal, among other things, that short-period mass fluctuations with a wavelength of 1 to 50 cm lead to a so-called moiré pattern, and that long-period mass variations with a wavelength of more than 5 m can cause relatively pronounced cross-stripes in the finished product. Accordingly, a fabric made of yarn of sample 1 (FIG. 3) would have cross-stripes and one made of yarn of sample 2 would have a moiré pattern. If hairiness or structure are examined instead of the mass variations, the same relationships basically apply, except that effects of periodic faults on the finished product are rather great with respect to hairiness and tend to be rather less with respect to structure.

Virtually all periodic faults lead to an uneven appearance in the finished products, to a so-called "cloudy character". With respect to non-periodic faults, the so-called imperfections, neps in particular have an extremely disturbing effect, because, as a rule, they have different reflection properties from fault-free yarn and, for example, absorb dye differently or not at all. The imperfections are recorded and counted in the USTER TESTER and are displayed and/or printed out separately according to types of fault, thick places, thin places and neps.

The signal from the measuring member of the FIG. 1 measuring module 4, which is reproduced in the graph of FIG. 2, and/or the signal processed by the evaluation and operating unit 2, for example the spectrogram of FIG. 3 and/or the number of neps, are used to generate an image of the woven or knitted fabric produced from the examined yarn on the video display unit 7. This image then directly shows the attendant the effects of the yarn faults found by the USTER TESTER on the finished product and thus allows a prognosis of the subsequent fabric image.

The simulation of the fabric image takes place in that the signal, which represent parameters associated with the volume or surface of the yarn are converted into grey values or color values and are assigned to one or more image spots (pixels), and in that these pixels are subsequently reproduced on the video display unit 7 and, if appropriate, also on the printer 3. In the simulation, the parameters can be displayed alternately or in any combination. For this reproduction, the "yarn guide" is variable. That is, the yarn can be wound spirally, as on a conventional display board, in which case the video display unit would reproduce the fabric image on the front side of the display board, or the display board can, as it were, be optionally made transparent and its front or rear side be superposed on one another. Alternately, the yarn can be guided in only one particular direction, for example from left to right, so that the thread is cut off at the right-hand of the board and is subsequently joined again on the left-hand side. Alternately, the yarn can be superposed crosswise, this corresponding to simulation of a woven fabric, or a knitted fabric. The image resolution can be selected as desired. For example, a plurality of threads lying next to one another can be combined, in which case the intensity of the image spots would correspond to the average value of the threads. Selective evaluations of the data are also possible, for example, by indicating only individual chimneys of the spectrogram or only the difference from the ideal spectrogram.

Two exemplary categories of signals are basically available as a starting point for calculating the grey values or color values. On the one hand, for a signal generated directly by the measuring member, according to the graph of FIG. 2, and, on the other hand, a signal which already represents the results of an evaluation carried out by the USTER TESTER; that is to say, for example, a spectrogram as shown in FIG. 3 or the results of a nep count. A signal of this second category would therefore represent average values or spreads of selected quantities relevant in textile terms. From the two signal categories, a yarn signal is then simulated for representation on the video display unit. For the simulation, particular characteristics can be emphasized by measures known from image processing, such as contrast accentuation, coloring and the like.

The following applies in general to the calculation:

l=F(y)

(l: brightness or color step;
y: mass, hairiness, structure, deviation from the average value and so forth)

When calculating from the first category of signals, that is to say from a graph such as that shown in FIG. 2, the following applies:

y=f(x)

(x: position in the longitudinal direction of the yarn), the y-values being taken directly from the graph.

When calculating from the second category of signals, the following applies to periodic faults (spectrogram):

$$y = \sum_{i=1}^{n} \left[ a_i \cdot \sin\left(\frac{\pi}{\lambda_i} \cdot x\right) \right]$$

(a; amplitude of the wavelength
i: index of the wavelength in the wavelength spectrogram
λ: wavelength
x: position in the longitudinal direction of the yarn)

The y-values therefore correspond to a reconstructed graph. Any chimneys in the spectrogram are either marked by hand or detected by means of the method such as that described in Swiss Patent application 2651/91, the disclosure of which is incorporated herein by reference. As an alternate to calculation by means of the given formula, a fast Fourier transform (FFT) can also be used.

In practice, the following preferably applies to the calculation of l:

$$y_1 = \sum_{i=1}^{n} \left[ a_i \cdot \left\{ 1 + \sin\left(\frac{\pi}{\lambda_i} \cdot x\right) \right\} \right]$$

$$l = k \cdot \sqrt{y_1} \text{ or } l = K \cdot y_1$$

($y_1$: deviation from the minimum value; for this, y is shifted so that $y_1$ is always positive)

(k, K: constant multiplier)

Rare faults occurring at random (that is, imperfections) are taken from the corresponding channel of the USTER TESTER and are represented in the image in terms of their intensity and frequency, the location of the respective image spots being determined by random numbers.

The question as to whether, for the faults occurring relatively frequently, one should proceed from the graph to image the real yarn on the video display unit, or whether one should proceed from the spectrogram and image a simulated yarn reconstructed from statistical values is now answered in favor of the spectrogram. This is because wavelengths recorded in the spectrogram are usually substantially lower in number than in the graph since a graph of high resolution would produce a very large quantity of data. There is therefore often no graph available which has the resolution necessary for representing the display image.

Moreover, it is questionable whether, for example, neps would be recognized in this image of the real yarn. In contrast, if the neps are taken from the nep channel and spread in the image in appropriate density and with suitable contrast accentuation, such as, for example, coloring, then they are recognized reliably even on the video display unit. In contrast, the continuous reconstruction of the graph from the spectrogram necessitates a substantially higher computing outlay than the direct conversion of the graph into brightness or color values.

Figure 4A:
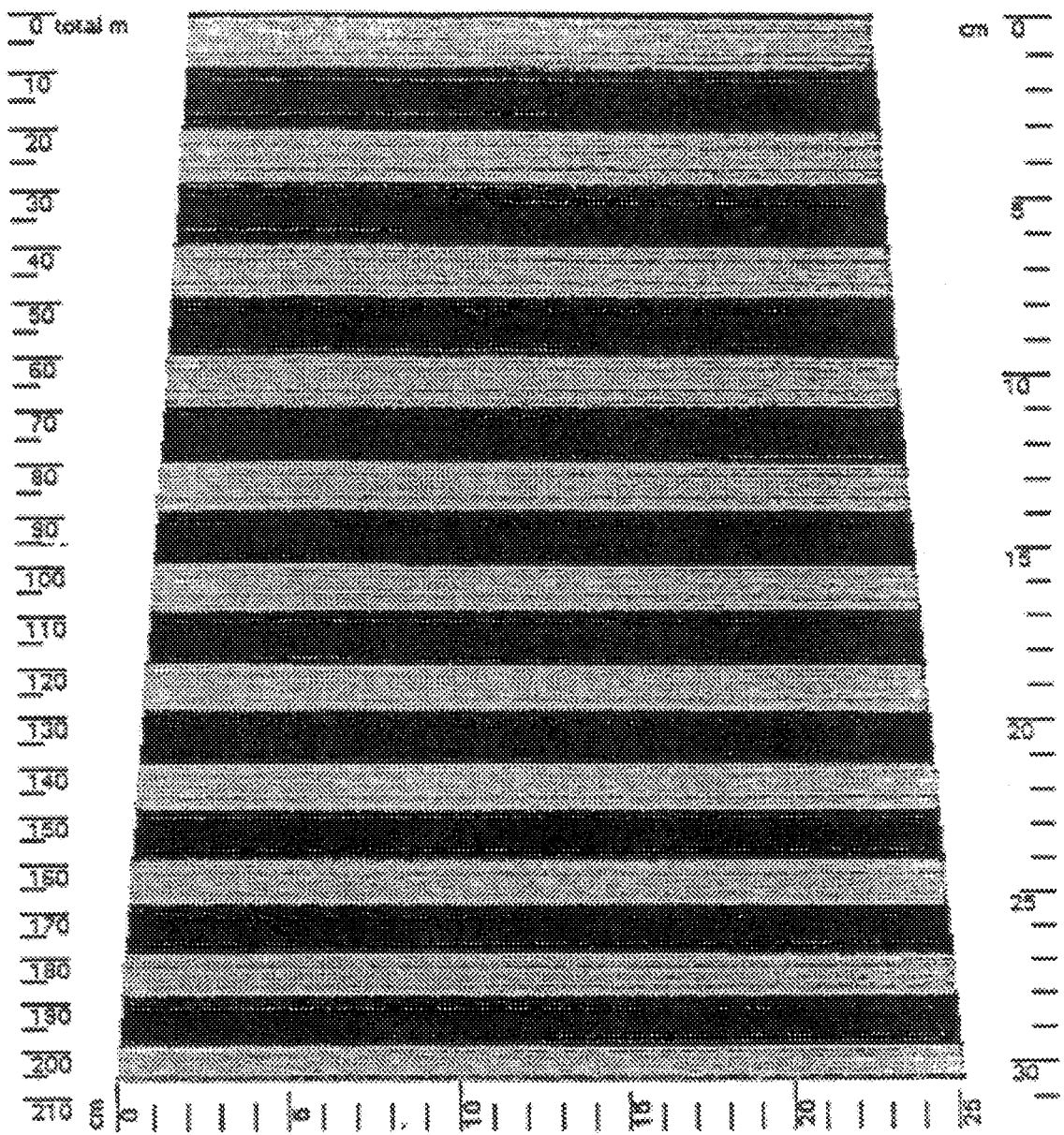
FIGS. 4a–4b show display-board simulations of the two samples of FIG. 3.
Figure 4B:
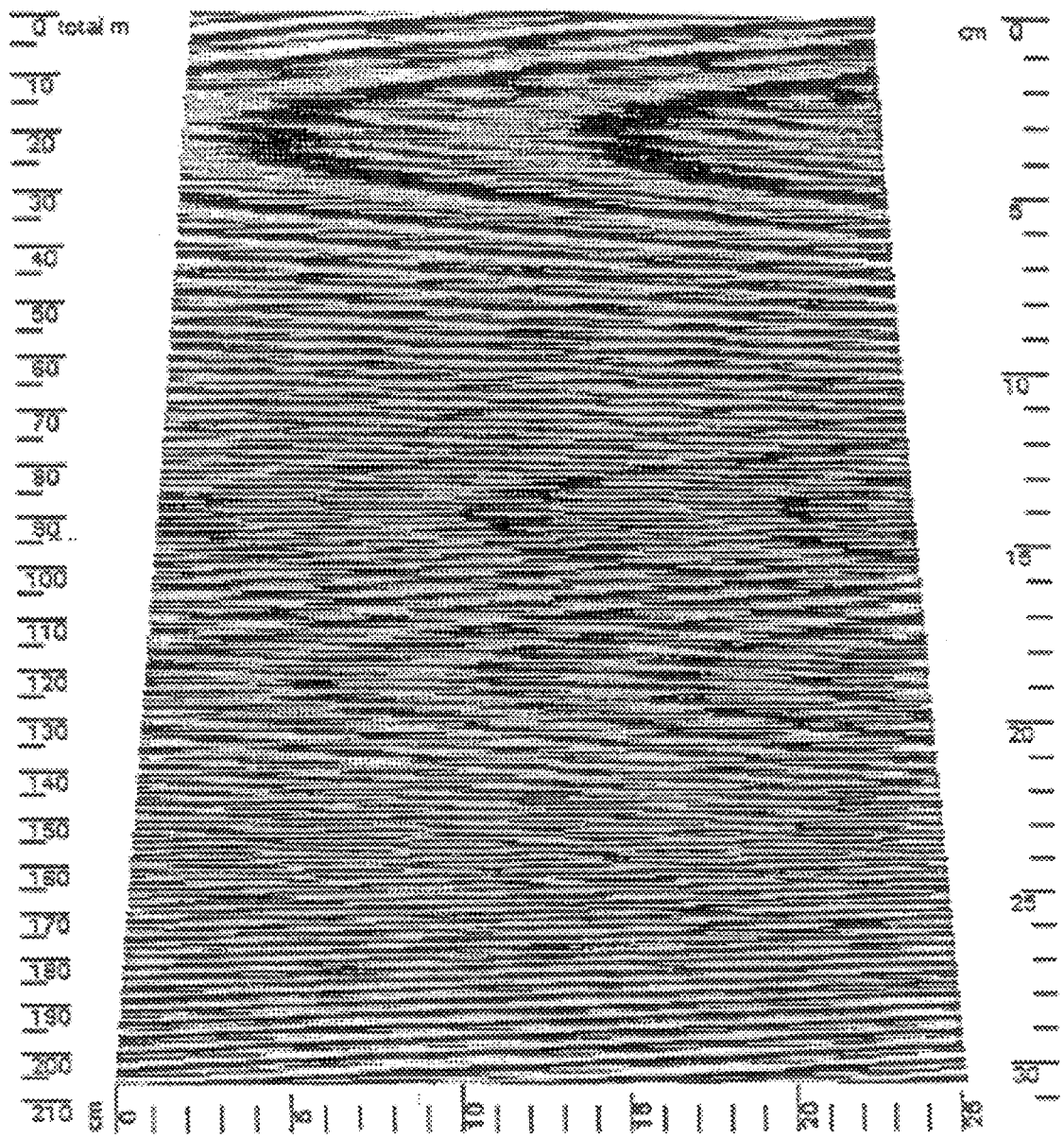

FIGS. 4a and 4b each show a display-board simulation, calculated from the spectrograms of FIG. 3, for each of the two samples 1 and 2. These simulations give a result, expected by the average person skilled in the art, with cross-stripes for sample 1 and with a moiré pattern for sample 2 which are caused by the periodic faults identified by the hatched chimneys in the two spectrograms. This result demonstrates the practicability of the method described.

In accordance with exemplary embodiments of the present invention, simulating the image of a fabric can thus be initiated by simulating a yarn (e.g. on video display screen). However, when simulating a yarn, several problems can arise depending on the specification or quality of the equipment used. This is especially true if less expensive and less performing equipment (e.g., video displays with reduced resolution) is used.

On a conventional display board wound with yarn, such as that described in the "Background" portion of the specification, the yarns are separated by a gap of approximately 1 mm in width. If the board is of black color, then the yarns are separated by black rows. When simulating such a display board with a low-cost video display (e.g., computer monitor), the reduced resolution of the monitor compared to the diameter of a yarn may not be sufficient to allocate one pixel or image spot to a point along a length of a specific yarn and one adjacent black pixel or image spot to the gap between the yarns. In such case, the typical linear structure of a conventional display board will be lost.

If the monitor resolution permits the allocation of one or more pixels to the width of the yarn and one or more pixels to the gap between the yarns, the linear structure of the board can be simulated well. However, the gaps between the yarn will reduce the average contrast of the simulation. For example, where the yarn is one pixel wide and the gap is two pixels wide then, even with a completely white yarn, the average brightness of the screen will only be 33%.

Thus, in accordance with alternate exemplary embodiments, multiple pixels on the display can be allocated to each point along a length of the yarn such that the intensity can be maintained constant over several consecutive pixels or image spots, or only gradually varied in intensity. As a result, the linear structure of the simulated yarn displayed on the monitor will be apparent.

Further, to improve the average contrast and brightness of a simulation wherein the width of a single yarn is represented using plural pixels, a typical yarn structure can be clearly displayed by changing, in a first step or time, only one of n columns or rows used to represent the yarn's width (e.g., from black over grey to white) and keeping the intensity of the remaining rows of columns black. With increasing intensity the remaining n–1 columns or rows can then be subsequently changed in intensity (e.g. from black to white). As a result, a yarn which is depicted horizontally across a display with plural rows of pixels will have a relatively bright center along the yarn axis, with a gradually decreasing brightness toward what would be considered the outer edges of the yarn.

For example, where a yarn is represented using 6 rows of pixels, the first row would be of relatively low intensity brightness, the second row would be of higher intensity brightness, and the third and fourth rows would be of even higher intensity brightness. The fifth and sixth rows would then be of brightness intensities corresponding to the second and first rows, respectively. The relative intensities of all rows, as well as lower and upper intensity limits, can be adjusted by the user while viewing the display until a satisfactory image of the yarn is achieved. The accepted simulation of the single yarn can then be used to establish brightness limits and relative intensities for use in subsequent simulation of a fabric.

In accordance with exemplary embodiments, increasing contrasts can also be used to accommodate a situation where the optical effect of the simulation is not equally good for different settings or values of the intensity, thereby degrading visual perception of the yarn. The optical effect of the simulation can be degraded if, for example, the screen is set for too high of an intensity, such that the image of the simulation may be deceiving. To address this potential degradation of the optical effect in accordance with an exemplary embodiment, a 100% black image spot can be allocated to a diameter of the yarn which is below the mean value by an exemplary amount of 35%, while a 100% white image spot can be allocated to a diameter exceeding the mean value by, for example, 35%. Additionally, yarn portions having diameters which are below or which exceed the mean diameter can be optically increased not only by increasing the intensity, but also by increasing the area covered in the picture as described previously. For example, thin places or thick places which represent faults in the yarn can be artificially extended lengthwise or widthwise over one or more rows or columns of pixels or image spots to highlight these places in the simulated yarn.

Thus, for an area of the yarn which is below a minimum diameter (for example, at a given location along the length of the yarn, a measured mass obtained from the FIG. 2 graph is below a predetermined threshold established relative to the mean value, such as a threshold of 35% below the mean value), the brightness of all pixels used to represent that portion of the yarn can be increased and the pixels can be represented as 100% white spots. Further, the pixels immediately adjacent the pixels used to represent that portion of the yarn, in a direction along the length of the yarn, can be increased in brightness to highlight the existence of a thin spot. Similarly, thick spots can be represented with an increased number of 100% white image spots.

In accordance with exemplary embodiments, display screens or video boards having any resolution can be used. However, screens or video boards which are only able to represent a reduced number of grey values (e.g. personal computers having so called VGA screens which only include a limited number of discrete grey values, such as 5 grey values) can degrade the quality of the simulation. Although available graphics-software often includes a mode which can be used to produce a fixed set of intermediate grey values, the use of this mode can, for single image points, create its own pattern which may interfere with the pattern to be created by the simulation. Similar problems can occur with the use of a black and white plotter or printer.

Accordingly, an improved simulation can be provided with the equipment described above if special attention is given to the foregoing effects. For example, rather than using a fixed set of intermediate color or grey values, interpolation between two given colors or grey values can be performed using known interpolation techniques, to in effect increase the number of available grey values which can be used to represent the yarn. Further, where each point along the length of yearn is represented by a block of pixels (for example, a 3×3 pixel array), a comparable effect can be achieved by randomly distributing black spots or pixels within each block, the distribution being performed with a density corresponding to the desired degree of blackening or attenuation using pixel patterns chosen to influence the apparent lightness or darkness of an area on the display. For example, the simulation can be improved by dividing the portion of a display used to represent each point of a single yarn into an area covering 5 to 20 pixels. The black spots in neighboring areas having different grey values or intensities can then be distributed with increased care (that is as regularly or uniformly as possible), and to make sure that the mean number or amount of such black spots distributed in each area corresponds exactly to the desired grey value in each area.

If a spectrogram as described with respect to FIG. 3 is used in the simulation for representing the yarn rather than using the original signal derived from the yarn (as illustrated in FIG. 2), then unwanted "moiré-effects" can appear when calculating the grey values for each pixel using known Fourier-Transformation formulae, such as the Inverse Discrete Fourier Transformation. To avoid these effects, the phase or frequency of signals in the spectrogram located between chimneys can be varied randomly within a range, such as a range corresponding to the distance between chimneys in the spectrogram. That is, the chimneys can be considered to define channels of the FIG. 3 spectrogram, with each channel being defined as a distance between two adjacent discrete chimney frequencies or frequency ranges for which the spectrogram is established.

Thus, frequencies associated with wavelengths located between the FIG. 3 chimneys can be randomly represented within the simulation with low intensity, while frequencies associated with the chimneys can be simulated with high intensity to ensure that they are adequately represented. When varying the phase, the phase can be varied until an analog frequency dispersion is obtained, because, as a consequence of varying the phase, the frequency will also vary. To obtain a clear picture of truly periodic faults represented by the chimneys of FIG. 3, such faults can be detected using known filter-algorithms and eliminated from the spectrogram. These periodic faults can then be subsequently added to the calculated yarn signal by adding sinusoidal functions or waves having an amplitude which corresponds to the chimneys.

When simulating yarn with the frequencies derived from a spectrogram, it is possible that other periodic waves are present which correspond to wavelengths of the spectrogram used for display purposes, but which do not have a frequency corresponding exactly to an integer multiple of the fundamental wave. This can be due, for example, to the fact that the resolution of the spectrogram is not infinite. If harmonic waves within a certain range of an integer multiple are forcedly given a frequency which is an exact integer multiple of the fundamental wave, then the image of the simulation will be improved since the intensity of the periodic faults will be further accentuated in the display.

When woven fabrics are to be simulated, the structure and the dimension of the fabric can have a large influence on the quality of the simulation to an extent to which the simulated fabric corresponds to the real fabric. The simulation can, for example, be improved by taking into account the width of the fabric when simulating the gap between adjacent yarns on the display relative to yarn width.

Thus, in accordance with exemplary embodiments, a fabric to be simulated on a display can be used to partition the display among pixels which will be used to represent yarn and pixels which will be used to represent the black board. After allocating the pixels accordingly, the intensity of each pixel used to represent the yarn in the fabric can be determined. For example, all frequencies of the spectrogram shown in FIG. 3, other than frequencies associated with the chimneys, can be used to allocate a given intensity to each pixel along the length of each yarn in the display. Afterwards, the intensities of pixels affected by the frequencies associated with the chimneys can be modified. Subsequently, pixels affected by imperfections in the yarn (e.g., neps) can be modified in intensity. As described previously, where a given pixel is determined to be associated with an imperfection, then one or more adjacent pixels associated with that pixel can be modified in intensity as well. For example, the total number of imperfections detected along a given length of the yarn can be calculated, and then randomly distributed in the display. After viewing the entire display of fabric, if brightness and/or contrast is inadequate, the display can be modified to further highlight imperfections by, for example, increasing the intensity of pixels used to represent chimneys and/or imperfections.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for assessing the effects of yarn faults on the appearance of fabrics produced from such yarn, said method comprising the steps of:

running an individual sample of the yarn lengthwise through a detector apparatus to produce signals indicative of variations in at least one yarn property along the running length of the individual sample;

processing said signals and producing image values therefrom, each of said image values being associated with a running length value of said yarn; and reproducing said image values as image spots in a sequence defined by said running length values.

2. A method for assessing the effect of yarn faults on woven or knitted fabrics produced from the respective yarn, by simulation of a fabric image, comprising the following steps:

a. examination of an individual sample along a running length of the yarn for parameters associated with at least one of the volume, the diameter and the surface of the yarn;

b. conversion of the said parameters into image values and assignment of these image values to image spots, each of said image spots being associated with said running length of the yarn; and c. reproduction of the image spots in a sequence defined by said running length of the yarn to generate an image which represents a simulation of a woven or knitted fabric produced from the examined yarn.

3. A method according to claim 2, wherein said parameters are designated by at least one of the mass, diameter, hairiness and structure of the yarn.

4. A method according to claim 3, wherein the conversion of said parameters takes place according to the formula l=F(y), l designating at least one of a brightness and a color step, and y the respective parameter.

5. A method according to claim 4, wherein graphs of directly measured variations of the said parameters are evaluated, and the values for the conversion are taken directly from the graphs.

6. A method according to claim 4 wherein selected quantities in textile terms are derived from the directly measured variations of the said parameters, and these derived quantities are used for the conversion, a yarn signal being simulated from these quantities in textile terms in order to reproduce the image spots.

7. A method according to claim 6 wherein for the simulation, particular characteristics are emphasized by measures known from image processing, such as contrast accentuation and coloring.

8. A method according to claim 7, wherein imperfections in the yarn are used for the conversion, the imperfections being represented in the image by means of the simulated yarn signal, with intensity and frequency corresponding to the intensity and frequency of the measured variations.

9. A method according to claim 7, wherein a wavelength spectrogram of the measured variations is used for the conversion, an examination of the wavelength spectrogram for chimney values projecting appreciably above an ideal spectrogram curve, being carried out.

10. A method according to claim 9, wherein the conversion takes place according to the formula $$y = \sum_{i=1}^{n} \left[ a_i \cdot \sin\left(\frac{\pi}{\lambda_i} \cdot x\right) \right]$$

$\lambda$ denoting the wavelength of a chimney, a its amplitude, i its index in the wavelength spectrogram, and x the position of the chimney in the longitudinal direction of the yarn sample, and y representing a reconstruction of the respective parameter.

11. An apparatus for assessing the effect of yarn faults on woven or knitted fabrics produced from the respective yarn, by a simulation of the fabric image, comprising:

a measuring member for determining parameters associated with at least one of the volume and the surface along a running length of an individual sample of the yarn;

a computer for converting said parameters into image values and for assigning the image values to image spots, each of said image spots being associated with said running length of the yarn;

at least one of a video display unit and a printer; and control means for reproducing the image spots on the video display unit or the printer in a sequence defined by said running length of the yarn for the purpose of simulating an image of a woven or knitted fabric to be produced from the yarn.

12. An apparatus according to claim 11, wherein the reproduced image spots represent a reconstructed image of the yarn.

13. An apparatus according to claim 11, wherein the reproduced image spots represent a simulation of the yarn which has been obtained by means of statistical examinations of quantities in textile terms of a yarn signal obtained during measurement of the yarn.

14. An apparatus according to claim 13, wherein the measuring member has a first sensor for determining at least one of the mass and diameter of the yarn.

15. An apparatus according to claim 12, wherein the measuring member has a first sensor for determining at least one of the mass and diameter of the yarn.

16. An apparatus according to claim 14, wherein the measuring member has at least one of a second and a third sensor respectively determining the hairiness and structure of the yarn.

17. An apparatus according to claim 15, wherein the measuring member has at least one of a second and a third sensor respectively determining the hairiness and structure of the yarn.

18. A method for assessing effects of yarn variations in a fabric to be knitted or woven from the yarn without producing said fabric, said method comprising the steps of:

examining an individual sample of the yarn to determine variations in a predetermined yarn parameter along a running length of the yarn;

identifying periodic and non-periodic faults in such individual yarn sample based on said step of examining; and simulating an image of a fabric to be produced using said yarn, said simulated fabric image including alterations in appearance due to said faults, said step of simulating further including the steps of:

converting said yarn parameter variations into image values, each of said image values being associated with said running length of the yarn; and assigning said image values to pixel locations in the simulated fabric image in a sequence defined by said running length of the yarn.

19. A method according to claim 18, wherein said image values are selected to be at least one of grey value intensities and color value.

20. A method according to claim 1, wherein said step of producing said image further includes a step of allocating at least one row of pixels in a display to the yarn, and allocating an adjacent row of pixels in the display to a gap between said yarn and an adjacent yarn.

21. A method according to claim 20 wherein said step of producing an image further includes a step of allocating a plurality of pixels to a width of the yarn, and gradually varying an intensity of said plurality of pixels to represent a given point along a length of the yarn.

22. A method according to claim 1, wherein said step of producing an image further includes a step of allocating at least one row of pixels in a display to simulate the yarn, and controlling an intensity of each pixel in proportion to a detected diameter of the yarn at a given location along a length of the yarn.

23. A method according to claim 22, wherein said step of producing an image further includes a step of increasing grey value intensity of pixels associated with yarn portions having diameters which are below and which exceed a mean diameter of the yarn.

24. A method according to claim 23, wherein said method of producing an image further includes a step of extending the number of pixels along a length of the yarn used to represent faults in the yarn.

25. A method according to claim 1, wherein said step of producing an image further includes a step of using at least one row of pixels in a display to simulate the yarn, wherein a grey value intensity of each pixel along a length of the yarn in the display is calculated by interpolating between available grey values of the display.

26. A method according to claim 1, wherein said step of producing an image further includes a step of using a block of pixels to represent each point along a length of the yarn on a display, and distributing pixels represented as black spots in each block to correspond to a desired grey value for that block.

27. A method according to claim 1, wherein said step of producing an image further includes a step of randomly representing frequencies associated with wavelengths which are located between wavelengths that correspond to periodic faults; and modifying said image to include waveforms which represent the periodic faults.

28. A method according to claim 2, wherein said step of reproduction further includes a step of allocating at least one row of pixels in a display to the yarn and allocating an adjacent row of pixels in the display to a gap between said yarn and an adjacent yarn.

29. A method according to claim 28, wherein said step of reproduction further includes a step of allocating a plurality of pixels to a width of the yarn, and gradually varying an intensity of said plurality of pixels to represent a given point along a length of the yarn.

30. A method according to claim 2, wherein said step of reproduction further includes a step of allocating at least one row of pixels in a display to simulate the yarn, and controlling an intensity of each pixel in proportion to a detected diameter of the yarn at a given location along a length of the yarn.

31. An apparatus according to claim 11, wherein said control means allocates at least one row of pixels in said video display unit to the yarn and allocates an adjacent row of pixels in the video display unit to a gap between said yarn and an adjacent yarn.

32. An apparatus according to claim 31, wherein said control means allocates a plurality of pixels to a width of the yarn, and gradually varies an intensity of said plurality of pixels to represent a given point along a length of the yarn.

33. An apparatus according to claim 11, wherein said control means allocates at least one row of pixels in said video display unit to simulate the yarn, and controls an intensity of each pixel in proportion to a detected diameter of the yarn at a given location along a length of the yarn.

34. A method according to claim 18, wherein said step of simulating further includes the step of allocating at least one row of pixels in a display to the yarn and allocating an adjacent row of pixels in the display to a gap between said yarn and an adjacent yarn.

35. A method according to claim 34, wherein said step of simulating further includes a step of allocating a plurality of pixels to a width of the yarn, and gradually varying an intensity of said plurality of pixels to represent a given point along a length of the yarn.

36. A method according to claim 18, wherein said step of simulating further includes a step of allocating at least one row of pixels in a display to simulate the yarn, and controlling an intensity of each pixel in proportion to a detected diameter of the yarn at a given location along the length of the yarn.

* * * * *